(12) United States Patent
Miyauchi

(10) Patent No.: US 10,196,165 B2
(45) Date of Patent: Feb. 5, 2019

(54) ROBOT SYSTEM, CONTAINER OPENING METHOD, AND MANUFACTURING METHOD OF OBJECT TO BE PROCESSED

(71) Applicant: KABUSHIKI KAISHA YASKAWA DENKI, Kitakyushu-shi (JP)

(72) Inventor: Kohei Miyauchi, Fukuoka (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 943 days.

(21) Appl. No.: 14/562,774

(22) Filed: Dec. 8, 2014

(65) Prior Publication Data

US 2015/0166208 A1 Jun. 18, 2015

(30) Foreign Application Priority Data

Dec. 13, 2013 (JP) ................................. 2013-258320

(51) Int. Cl.
*B65B 69/00* (2006.01)
*B25J 9/16* (2006.01)
*G01N 35/00* (2006.01)
*G01N 35/04* (2006.01)

(52) U.S. Cl.
CPC ............. *B65B 69/00* (2013.01); *B25J 9/1612* (2013.01); *G01N 35/0099* (2013.01); *G01N 2035/0405* (2013.01); *Y10S 901/02* (2013.01); *Y10S 901/31* (2013.01)

(58) Field of Classification Search
CPC ....... B65B 69/00; B25J 9/1612; B25J 9/1682; G01N 35/0099; G01N 2035/0405; Y10S 901/02; Y10S 901/31; B67B 7/18; B67B 7/182

USPC .......................... 901/8, 15, 18; 53/492, 381.4
See application file for complete search history.

(56) References Cited

U.S. PATENT DOCUMENTS

| 4,762,455 A * | 8/1988 | Coughlan .................. B25J 3/04 376/248 |
| 4,780,047 A * | 10/1988 | Holt .......................... B25J 3/04 414/730 |
| 2003/0061911 A1 | 4/2003 | Niwayama et al. |

(Continued)

FOREIGN PATENT DOCUMENTS

| CN | 1689958 | 11/2005 |
| CN | 202429976 U | 9/2012 |

(Continued)

OTHER PUBLICATIONS

Extended European Search Report for corresponding EP Application No. 14195367.9-1712, dated Jun. 12, 2015.

(Continued)

*Primary Examiner* — Thanh Truong
*Assistant Examiner* — Thomas Wittenschlaeger
(74) *Attorney, Agent, or Firm* — Mori & Ward, LLP

(57) ABSTRACT

A robot system includes a robot, a hand attached to the robot, and a controller configured to control operation of the robot. The controller includes an initial control unit configured to rotate the hand in a state where the hand holds the screw cap tightened onto a conical tube in a first attitude, and a normal control unit configured to rotate the hand in a state where the hand holds the screw cap in a second attitude different from the first attitude after the hand is operated by the initial control unit.

20 Claims, 11 Drawing Sheets

(56) References Cited

U.S. PATENT DOCUMENTS

| | | | |
|---|---|---|---|
| 2011/0185556 A1* | 8/2011 | Hirano | B25J 9/0084 29/428 |
| 2012/0134896 A1* | 5/2012 | Chiyajo | G01N 35/0099 422/549 |
| 2014/0106386 A1 | 4/2014 | Umeno et al. | |

FOREIGN PATENT DOCUMENTS

| | | |
|---|---|---|
| EP | 1512500 A2 | 3/2005 |
| JP | 61-201791 U | 12/1986 |
| JP | 07-088790 | 4/1995 |
| JP | 2003-094374 | 4/2003 |
| JP | 2004-028783 | 1/2004 |
| JP | 2013-009618 | 1/2013 |

OTHER PUBLICATIONS

Michelman et al., "Forming complex dextrous manipulations from task primitives", Robotics and Automation, 1994. Proceedings., 1994 IEEE International Conference on San Diego, CA, USA May 8-13, 1994, Los Alamitos, CA, USA,IEEE Comput. Soc, May 8, 1994, pp. 3383-3388, XP010097531, DOI: 10.1109/ROBOT.1994. 351050 ISBN: 978-0-8186-5330-8.

Steffen et al., "Bio-inspired Motion Strategies for a Bimanual Manipulation Task", Humanoid Robots (Humanoids), 2010 IOTH IEEE-RAS International Conference on, IEEE, Piscataway, NJ, USA, Dec. 6, 2010, pp. 625-630, XP031848656, ISBN: 978-1-4244-8688-5.

Karnati et al., "Bioinspired Sinusoidal Finger Joint Synergies for a Dexterous Robotic Hand to Screw and Unscrew Objects With Different Diameters", IEEE / ASME Transactions on Mechatronics, IEEE Service Center, Piscataway, NJ, US, vol. 18, No. 2, Apr. 1, 2013, pp. 612-623, XP011487019,ISSN: 1083-4435, DOI: 10.1109/TMECH.2012.2222907.

Chinese Office Action for corresponding CN Application No. 201410748037.2, dated Apr. 5, 2016.

Japanese Office Action for corresponding JP Application No. 2013-258320, dated Dec. 1, 2015.

European Office Action for corresponding EP Application No. 14195367.9—1018, dated Nov. 26, 2018.

* cited by examiner

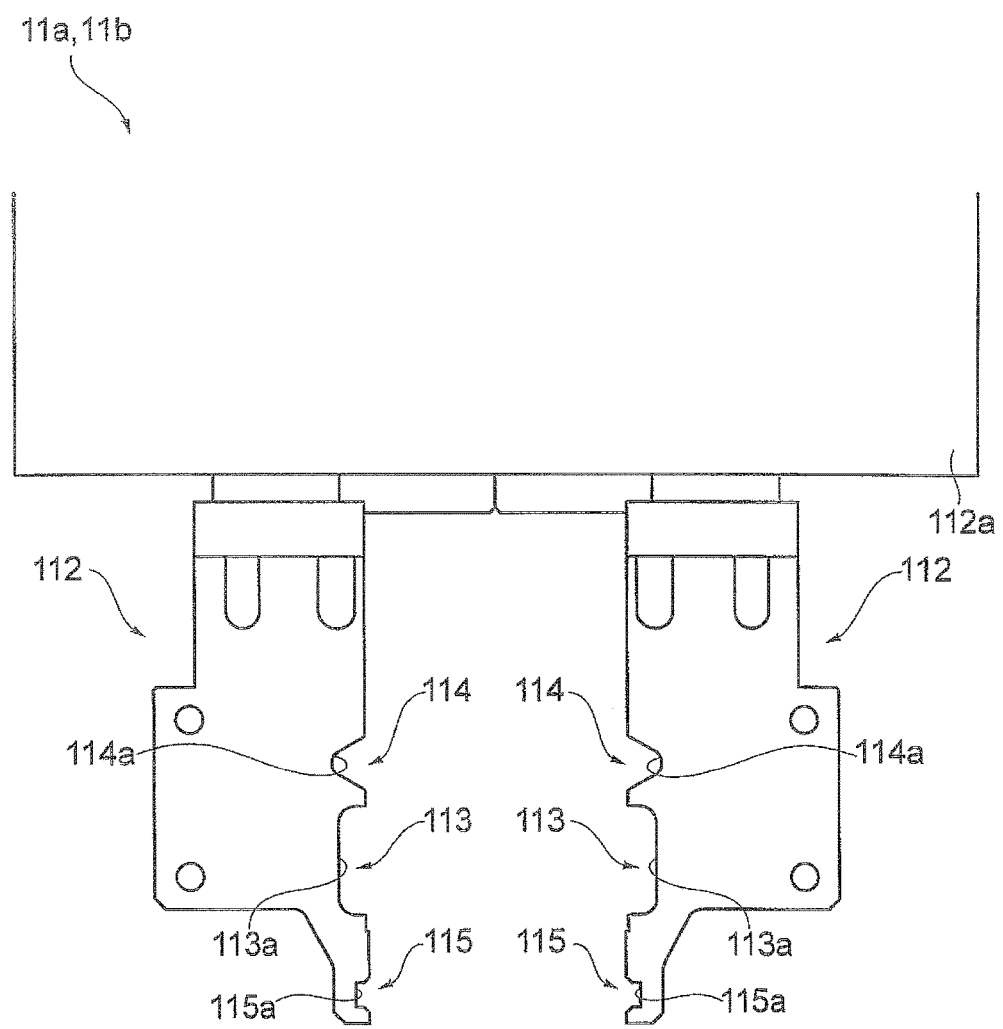

ROBOT SYSTEM, CONTAINER OPENING METHOD, AND MANUFACTURING METHOD OF OBJECT TO BE PROCESSED

CROSS-REFERENCE TO RELATED APPLICATION

This application is based upon and claims the benefit of priority from Japanese Patent Application No. 2013-258320, filed Dec. 13, 2013, the entire contents of which are incorporated herein by reference.

BACKGROUND

1. Field

The disclosure relates to a robot system, a container opening method, and a manufacturing method of an object to be processed.

2. Description of the Related Art

A robot system described in JP 2004-28783 A performs opening operation by moving an arm and a hand attached to the distal end of the arm closer to a screw cap in a direction orthogonal to the upper surface of the screw cap, holding the screw cap by the distal end of the hand, and rotating the screw cap.

SUMMARY

A robot system according to the disclosure includes: a first robot; a first hand attached to the first robot; and a control device configured to control operation of the first robot. The control device includes: an initial control unit configured to rotate the first hand in a state where the first hand holds a screw cap tightened onto a predetermined container in a first attitude; and a normal control unit configured to rotate the first hand in a state where the first hand holds the screw cap in a second attitude different from the first attitude after the first hand is operated by the initial control unit.

A container opening method according to the disclosure includes: rotating a first hand, which is attached to a first robot, in a state where the first hand holds a screw cap tightened onto a predetermined container in a first attitude; and thereafter rotating the first hand in a state where the first hand holds the screw cap in a second attitude different from the first attitude.

A manufacturing method of an object to be processed according to the disclosure is a manufacturing method of an object to be processed including a container body and a screw cap tightened onto the container body. The method includes: rotating a first hand, which is attached to a first robot, in a state where the first hand holds the screw cap in a first attitude; and thereafter rotating the first hand in a state where the first hand holds the screw cap in a second attitude different from the first attitude.

BRIEF DESCRIPTION OF THE DRAWINGS

FIG. 3 is a front view of hands included in the robot system illustrated in FIG. 1;

DETAILED DESCRIPTION

Hereinafter, an embodiment will be described with reference to the accompanying drawings. The same reference signs are used throughout the drawings to refer to the same or like parts, and the same description will not be repeated.

A robot system according to the present embodiment is configured to perform opening operation of a screw cap tightened onto a predetermined container. As a predetermined container, for example, a centrifuge tube and a conical tube may be used. Hereinafter, an example for opening a screw cap of a conical tube storing a sample including blood, a part of tissue, etc. (hereinafter, simply referred to as a sample) for analyzing or testing the sample.

Figure 1:
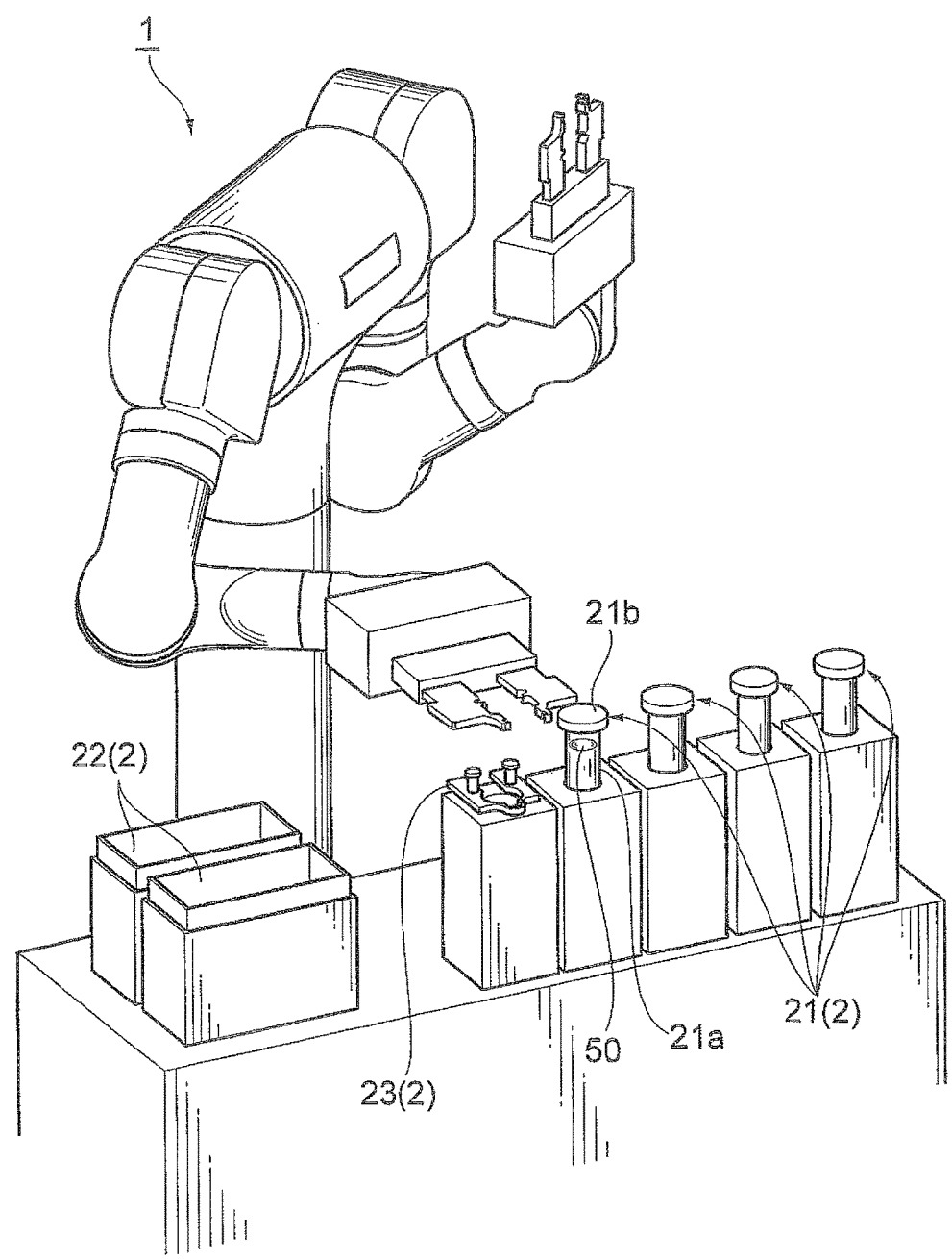
FIG. 1 is a perspective view of a robot system according to an embodiment and a processing device.

FIG. 1 is a perspective view of the robot system according to the present invention and a processing device. The robot system 1 and the processing device 2 are placed, for example, in a cleaning room in which the air cleaning degree is secured and are used for analyzing and testing a sample 50.

The processing device 2 includes a conical tube 21 (an object to be processed), a storage container 22, and a holding tool 23. The conical tube 21 includes a storage part 21a (container body) and a screw cap 21b. The storage part 21a has a space therein. In the storage part 21a, an opening communicating with the inner space is formed. On the outer peripheral surface around the opening of the storage part 21a, a male screw is formed. On the inner peripheral surface of the screw cap 21b, a female screw is formed. Engagement of the male screw of the storage part 21a and the female screw of the screw cap 21b makes the screw cap 21b attached to the storage part 21a. The storage container 22 stores a sample 50 after opening operation of the screw cap 21b to be described later. The holding tool 23 is used when a robot (to be described later) of the robot system 1 holds the conical tube 21. The holding tool 23 will be described in detail later.

Figure 2A:
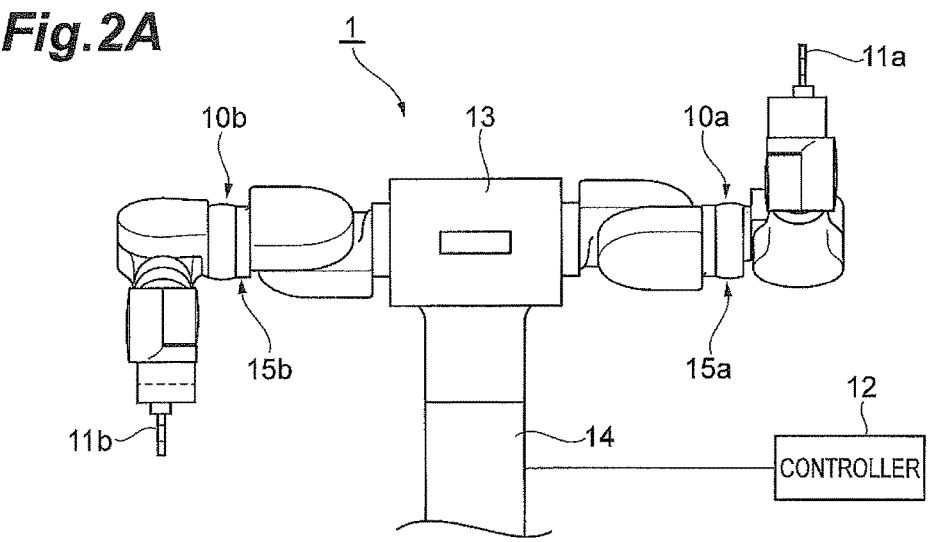
FIG. 2A is a front view of the robot system illustrated in FIG. 1.
Figure 2B:
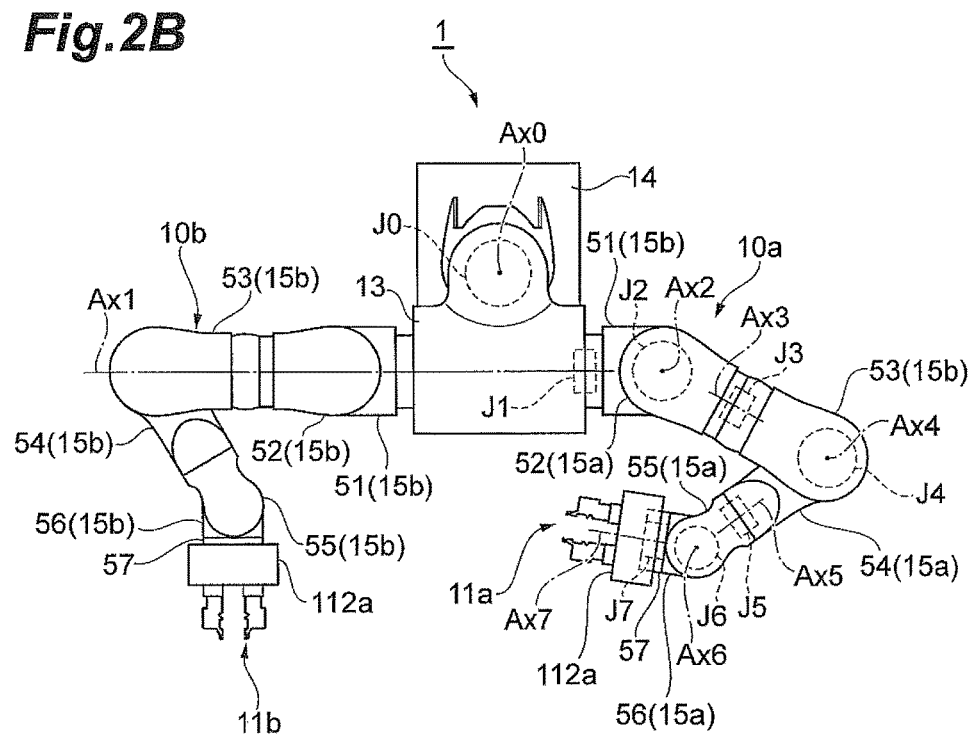
FIG. 2B is a plan view of the robot system illustrated in FIG. 1.

The robot system 1 will be described in detail also with reference to FIG. 2. FIG. 2A is a front view of the robot system 1 illustrated in FIG. 1, and FIG. 2B is a plan view of the robot system 1 illustrated in FIG. 1. The robot system 1 includes robots 10a (first robot) and 10b (second robot), hands 11a (first hand) and 11b (second hand), a controller 12, a body 13, and a base 14.

The base 14 is fixed on an installation surface using, for example, an anchor bolt (not illustrated). The body 13 is mounted on the base 14. The body 13 is a common body, to which the robot 10a and the robot 10b are attached. The body 13 includes a joint J0 provided with an actuator that is rotary driven around a rotation axis Ax0, which is orthogonal to the installation surface of the base 14. The body 13 is installed on the base 14 such that the body 13 is turnable with respect to the base 14 through the joint J0 and turns along a direction that is substantially parallel to the installation surface of the base 14 by driving the actuator provided to the joint J0.

The robots 10a and 10b are operated based on operation instructions from the controller 12. An operation instruction is a command that is a program for operating a robot or a job that is a set of programs for operating a robot. The robot 10a is configured to hold and rotate the screw cap 21b of the conical tube 21 in opening processing to be described later. The robot 10b is configured to fix the conical tube 21 to a predetermined operation position in the opening processing to be described later. The robot 10a includes an arm 15a. The robot 10b includes an arm 15b. The arms 15a and 15b are manipulators inside which actuators are provided. The arms 15a and 15b are respectively supported by the body 13.

Each of the arms 15a and 15b includes, from the base end side to the distal end side, a shoulder 51, a first upper arm 52, a second upper arm 53, a lower arm 54, a first wrist 55, a second wrist 56, and a flange 57.

The shoulder 51 is connected to the body 13 through a first joint J1, to which an actuator is provided. The shoulder 51 rotates around a rotation axis Ax1, which is substantially parallel to the installation surface of the base 14, corresponding to driving of the actuator provided to the first joint J1. The first upper arm 52 is connected to the shoulder 51 through a second joint J2, to which an actuator is provided. The first upper arm 52 rotates around a rotation axis Ax2, which is orthogonal to the rotation axis Ax1, corresponding to driving of the actuator provided to the second joint J2. The second upper arm 53 is connected to the first upper arm 52 through a third joint J3, to which an actuator is provided. The second upper arm 53 rotates around a rotation axis Ax3, which is orthogonal to the rotation axis Ax2, corresponding to driving of the actuator provided to the third joint J3. The lower arm 54 is connected to the second upper arm 53 through a fourth joint J4, to which an actuator is provided. The lower arm 54 rotates around a rotation axis Ax4, which is orthogonal to the rotation axis Ax3 corresponding to driving of the actuator provided to the fourth joint J4.

The first wrist 55 is connected to the lower arm 54 through a fifth joint J5, to which an actuator is provided. The first wrist 55 rotates around a rotation axis Ax5, which is orthogonal to the rotation axis Ax4, corresponding to driving of the actuator provided to the fifth joint J5. The second wrist 56 is connected to the first wrist 55 through a sixth joint J6, to which an actuator is provided. The second wrist 56 rotates around a rotation axis Ax6, which is orthogonal to the rotation axis Ax5, corresponding to driving of the actuator provided to the sixth joint M. The flange 57 is connected to the second wrist 56 through a seventh joint J7, to which an actuator is provided. The flange 57 rotates around a rotation axis Ax7, which is orthogonal to the rotation axis Ax6, corresponding to driving of the actuator provided to the seventh joint J7. As described above, the arms 15a and 15b respectively have seven axes: the rotation axes Ax1 to Ax7. Thus, the robots 10a and 10b are seven-axis robots.

The hand 11a is an end effector, which is attached to the arm 15a of the robot 10a. The hand 11b is an end effector, which is attached to the arm 15b of the robot 10b. More specifically, the hands 11a and 11b are attached to the distal ends of the flanges 57. The hands 11a and 11b are rotated by the flange 57 rotating around the rotation axis Ax1 described above.

The hands 11a and 11b are described in detail also with reference to FIG. 3. FIG. 3 is a front view of the hands 11a and 11b included in the robot system 1 illustrated in FIG. 1. The hands 11a and 11b include a hand body 112a and a pair of holding members 112 provided at the distal end of the hand body 112a. The holding members 112 can move in directions away from/closer to each other, allowing increase/decrease (adjustment) of the relative distance between them. A mechanism for allowing increase/decrease of the relative distance between them is stored inside the hand body 112a. As a mechanism for increasing/decreasing (adjusting) the relative distance between the holding members 112, a rack and pinion or a ball screw can be used for simple configuration, but other mechanisms can be also used. Each of the holding members 112 includes a first concave portion 113, a second concave portion 114, and a claw 115, and respective ones of the holding members 112 are positioned opposite to each other.

The first concave portion 113 is formed between the second concave portion 114 and the claw 115. The first concave portion 113 is concave on the inner side of the holding member 112 in a direction intersecting the extending direction of the holding member 112. A bottom 113a of the first concave portion 113 and a bottom 114a of the second concave portion 114 each have a concave shape, and the flat portion of the bottom 113a is longer than that of the bottom 114a. Therefore, the first concave portions 113 can hold a relatively large member between the opposing bottoms 113a. In addition, the bottom 113a of the first concave portion 113 has a long flat portion and thus has a large surface in contact with a member to be held, easily applying force to a member to be held.

The second concave portion 114 is formed closer to the base end side of the holding member 112 compared to the first concave portion 113. The second concave portion 114 is a portion, which is concave on the inner side of the holding member 112 in a direction intersecting the extending direction of the holding member 112. The bottom 114a of the second concave portion 114 and the bottom 113a of the first concave portion 113 each have a concave shape, and the flat portion of the bottom 114a is shorter than that of the bottom 113a. Therefore, the second concave portions 114 can hold a relatively small member between the opposing bottoms 114a.

The claws 115 are provided at the distal end of the holding members 112. Each of the claws 115 has a cutout 115a on its distal end side. The cutout 115a formed in the claw 115 increases holding force for holding a member.

With reference to FIG. 2 again, the controller 12 is a control device configured to control operation of the robots 10a and 10b. More specifically, the controller 12 is connected to the actuators of the robots 10a and 10b through cable harnesses (not illustrated). The controller 12 drives the actuators by outputting operation instructions so as to control operation of the robots 10a and 10b. The function of the controller 12 will be described in detail also with reference to FIG. 4.

Figure 4:
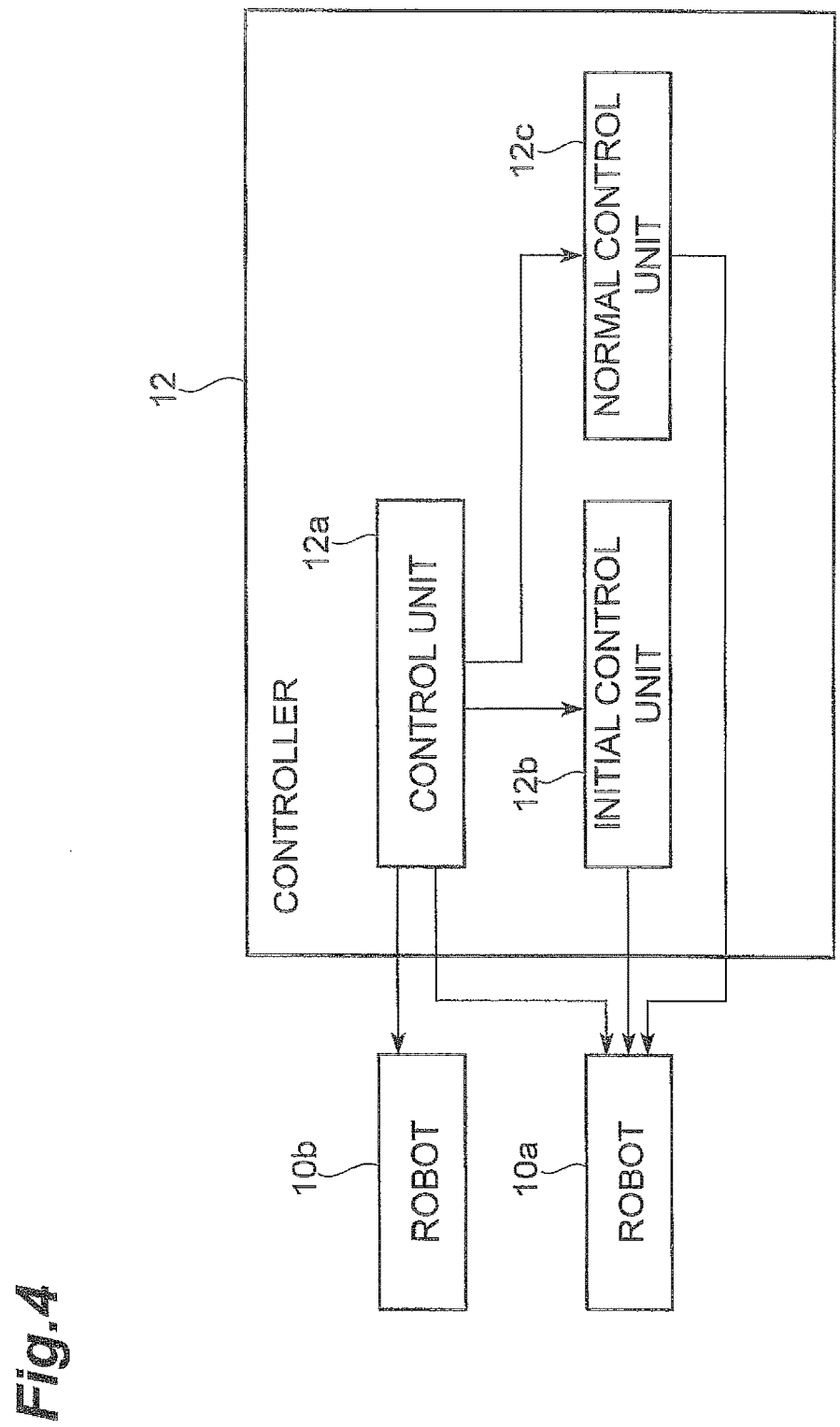
FIG. 4 is a drawing illustrating functional blocks of a controller.

FIG. 4 is a drawing illustrating functional blocks of the controller 12. As illustrated in FIG. 4, the controller 12 includes a control unit 12a, an initial control unit 12b, and a normal control unit 12c. The controller 12 performs pre-opening processing, opening processing, and post-opening processing as processing related to the opening operation of the screw cap 21b in conjunction with the robots 10a and 10b. The pre-opening processing and the post-opening processing are performed by the control unit 12a. The opening processing is performed by the initial control unit 12b and the normal control unit 12c. Hereinafter, a case where the control unit 12a etc. outputs an operation instruction to the robots 10a and 10b for each part of processing of the robots 10a and 10b will be described for convenience of explanation. However, the control unit 12a etc. may output one job (operation instruction) for the whole processing related to the opening operation.

The control unit 12a controls operation of the robots 10a and 10b by outputting operation instructions related to the pre-opening processing and the post-opening processing to the robots 10a and 10b. Hereinafter, the processing of the control unit 12a during the pre-opening processing and the post-opening processing will be described.

The pre-opening processing is performed at a stage preceding opening of the screw cap 21b by the robots 10a and 10b. The control unit 12a outputs an operation instruction to the robot 10b causing the robot 10b to hold the conical tube 21. When the conical tube 21 is provided in a plurality, the control unit 12a causes the robot 10b to hold a predetermined one of the conical tubes 21. The control unit 12a also outputs an operation instruction to the robot 10b causing the robot 10b to mount the conical tube 21 on the holding tool 23.

Figure 5:
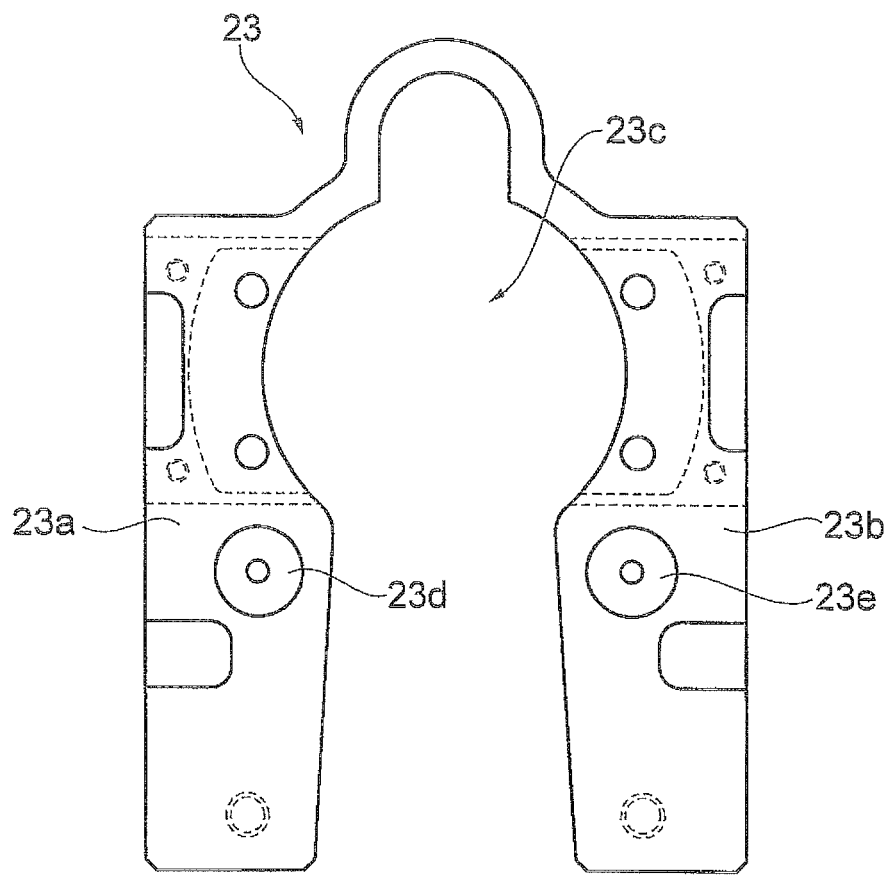
FIG. 5 is a plan view of a holding tool.
Figure 6:
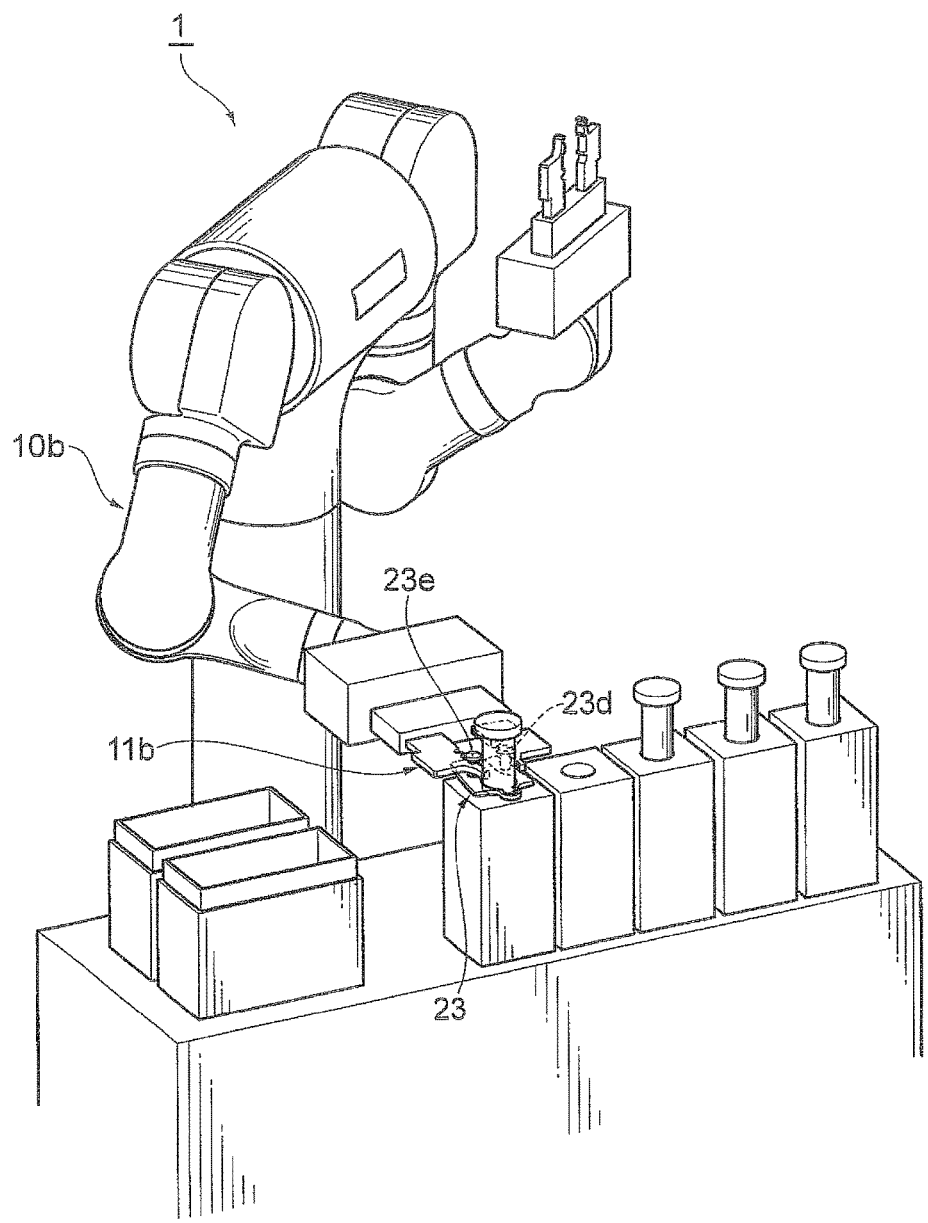
FIG. 6 is a perspective view illustrating a use state of the holding tool.

The holding tool 23 will now be described in detail with reference to FIGS. 5 and 6. FIG. 5 is a plan view of the holding tool 23. FIG. 6 is a perspective view illustrating a use state of the holding tool 23. The holding tool 23 includes opposing side walls 23a and 23b. Inner sides of the side walls 23a and 23b each have a concave shape such that the opposing concave shapes form a substantially circular insertion space 23c. In the insertion space 23c, the conical tube 21 is inserted. The holding tool 23 also has a protrusion 23d protruding from one end side of a side wall 23a in a direction orthogonal thereto and a protrusion 23e protruding from one end side of a side wall 23b in a direction orthogonal thereto. The protrusions 23d and 23e protrude to an extent allowing the hand 11b to hold the protrusions 23d and 23e. The outer sides of the protrusions 23d and 23e of the holding tool 23 are held by the hand 11b in a state where the conical tube 21 is inserted in the insertion space 23c. Holding the outer side of the protrusions 23d and 23e moves the side walls 23a and 23b in directions toward each other, thus narrowing the insertion space 23c compared with a state before the holding. As a result, the conical tube 21 can be fixed between the side walls 23a and 23b.

The holding tool 23 is used as follows. At a predetermined position where the holding tool 23 is mounted, a member for supporting the conical tube 21 inserted in the insertion space 23c is provided. First, the conical tube 21 held by the robot 10b is inserted in the insertion space 23c of the holding tool 23 and supported by the member for supporting the conical tube 21. Then, as illustrated in FIG. 6, the robot 10b holds the protrusions 23d and 23e with the hand 11b. This narrows the insertion space 23c, and thus fixes the conical tube 21 between the side walls 23a and 23b, enabling to hold the conical tube 21.

The control unit 12a outputs an operation instruction to the robot 10b causing the robot 10b to move to the predetermined operation position and stop at the operation position while the robot 10b holds the conical tube 21. At the predetermined operation position, the robot 10b can operate safely considering the position of the processing device 2 and other processing. The control unit 12a also outputs an operation instruction to the robot 10b causing the robot 10b to perform stirring processing of a sample 50 stored in the conical tube 21. The stirring processing is to stir the sample 50, and may be processing for holding the conical tube 21 upside down for about eight to twelve seconds, for example. When the stirring processing is completed, the control unit 12a outputs information that indicates completion of the stirring processing to the initial control unit 12b and the normal control unit 12c. The operation of the control unit 12a during the pre-opening processing has been described. Next, the operation of the control unit 12a during the post-opening processing will be described.

The post-opening processing is performed after the robots 10a and 10b have completed the opening of the screw cap 21b. The control unit 12a outputs an operation instruction to the robot 10b causing the robot 10b to transfer the sample 50 stored in the conical tube 21 to the storage container 22. The control unit 12a also outputs an operation instruction to the robot 10a causing the robot 10a to tighten the screw cap 21b onto the conical tube 21 after the transfer of the sample 50. The control unit 12a also outputs an operation instruction to the robot 10b causing the robot 10b to move the conical tube 21 after the transfer of the sample 50 back to the position of the conical tube 21 before the pre-opening processing.

Figure 7:
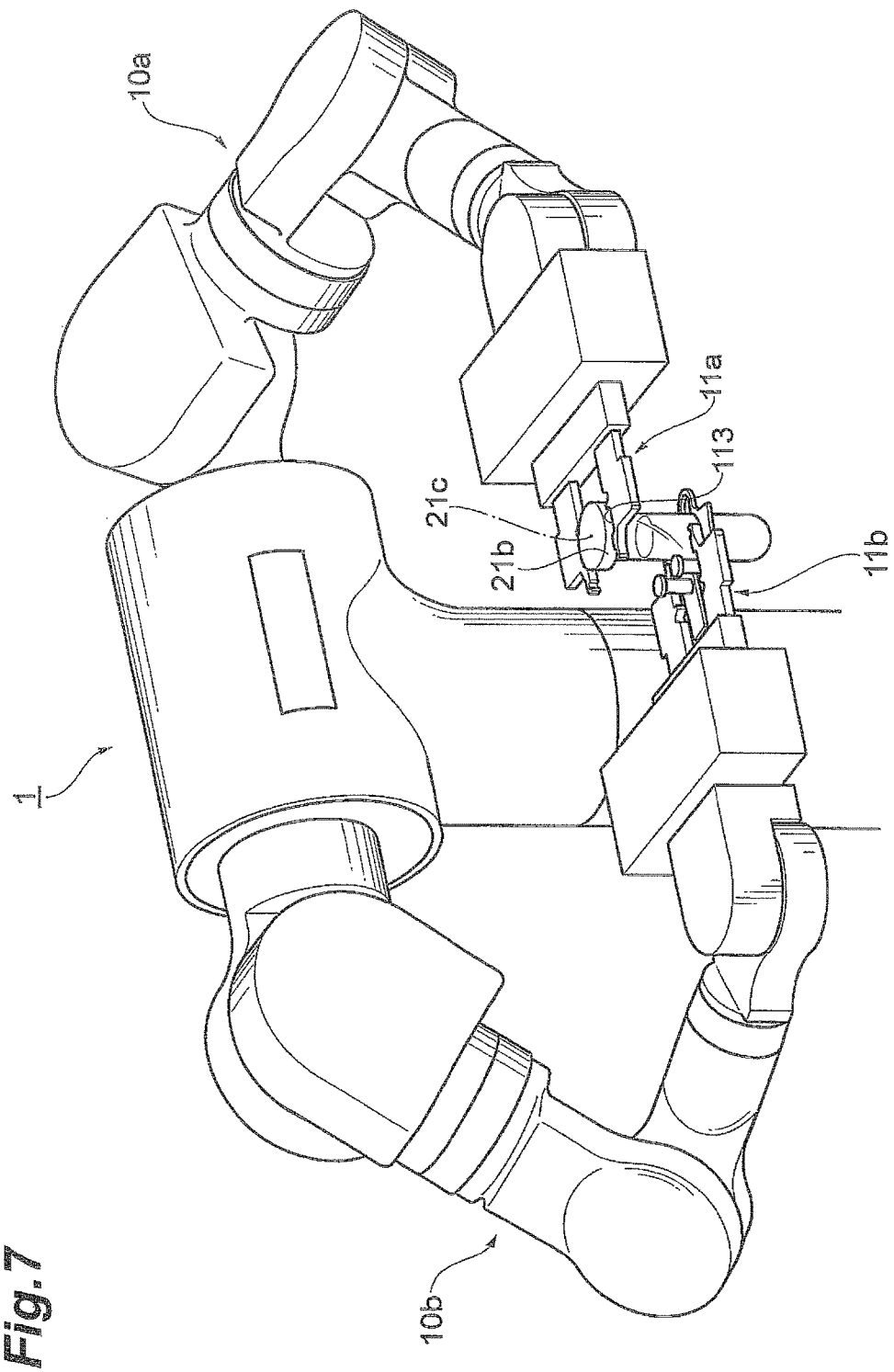
FIG. 7 is a perspective view illustrating the robot system during initial control.
Figure 8:
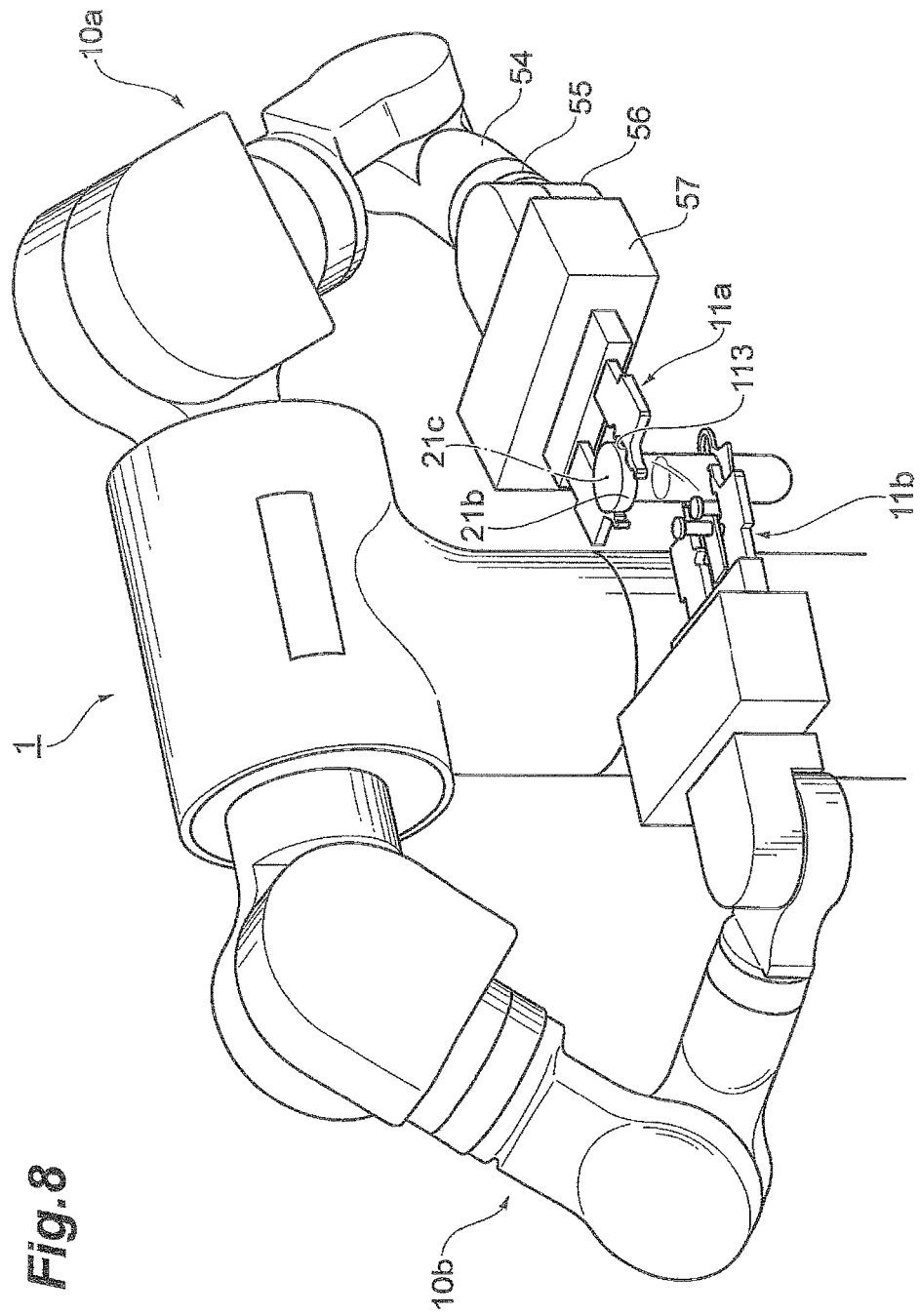
FIG. 8 is a perspective view of the robot system during the initial control.
Figure 9:
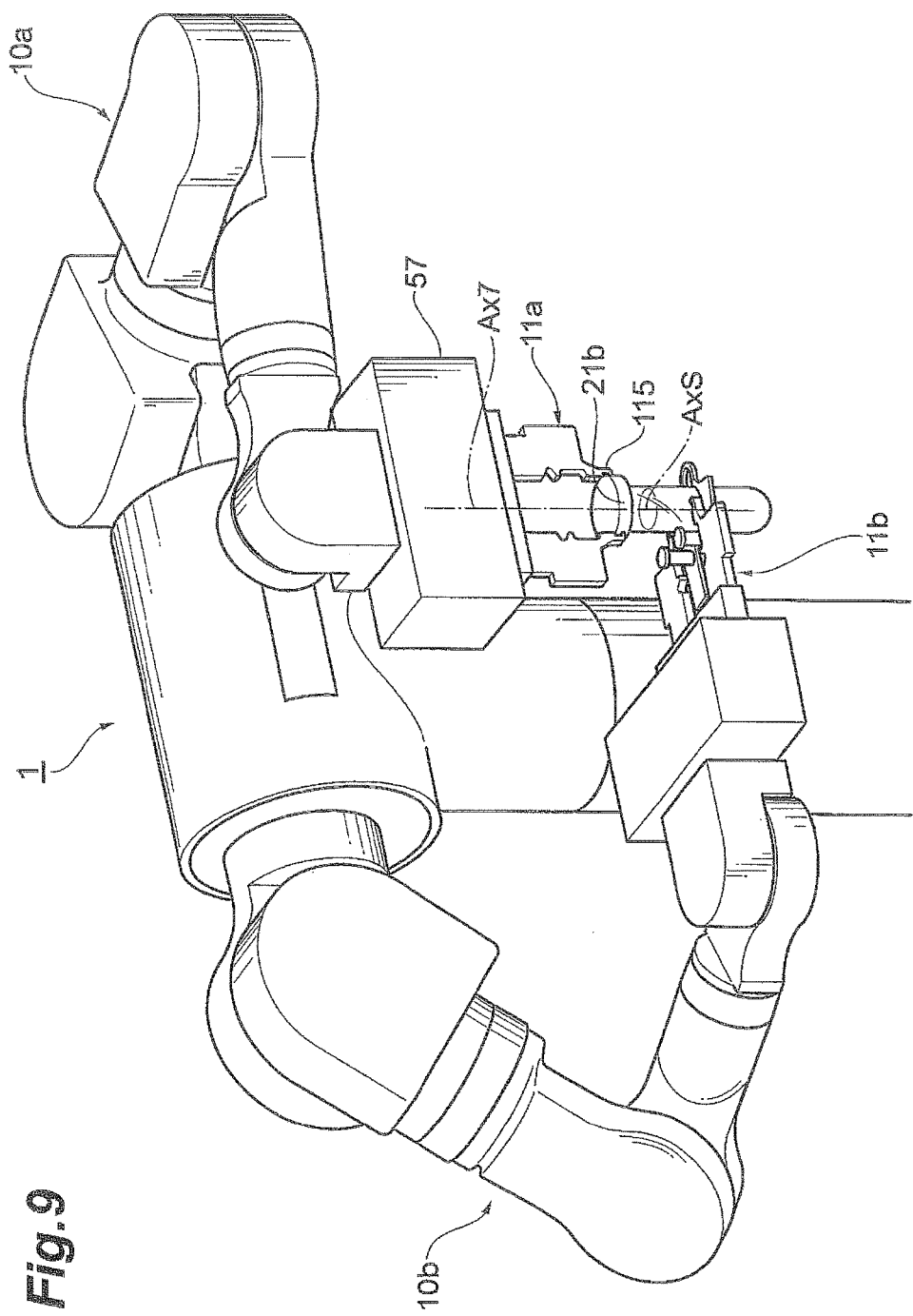
FIG. 9 is a perspective view illustrating the robot system during normal control.
Figure 10:
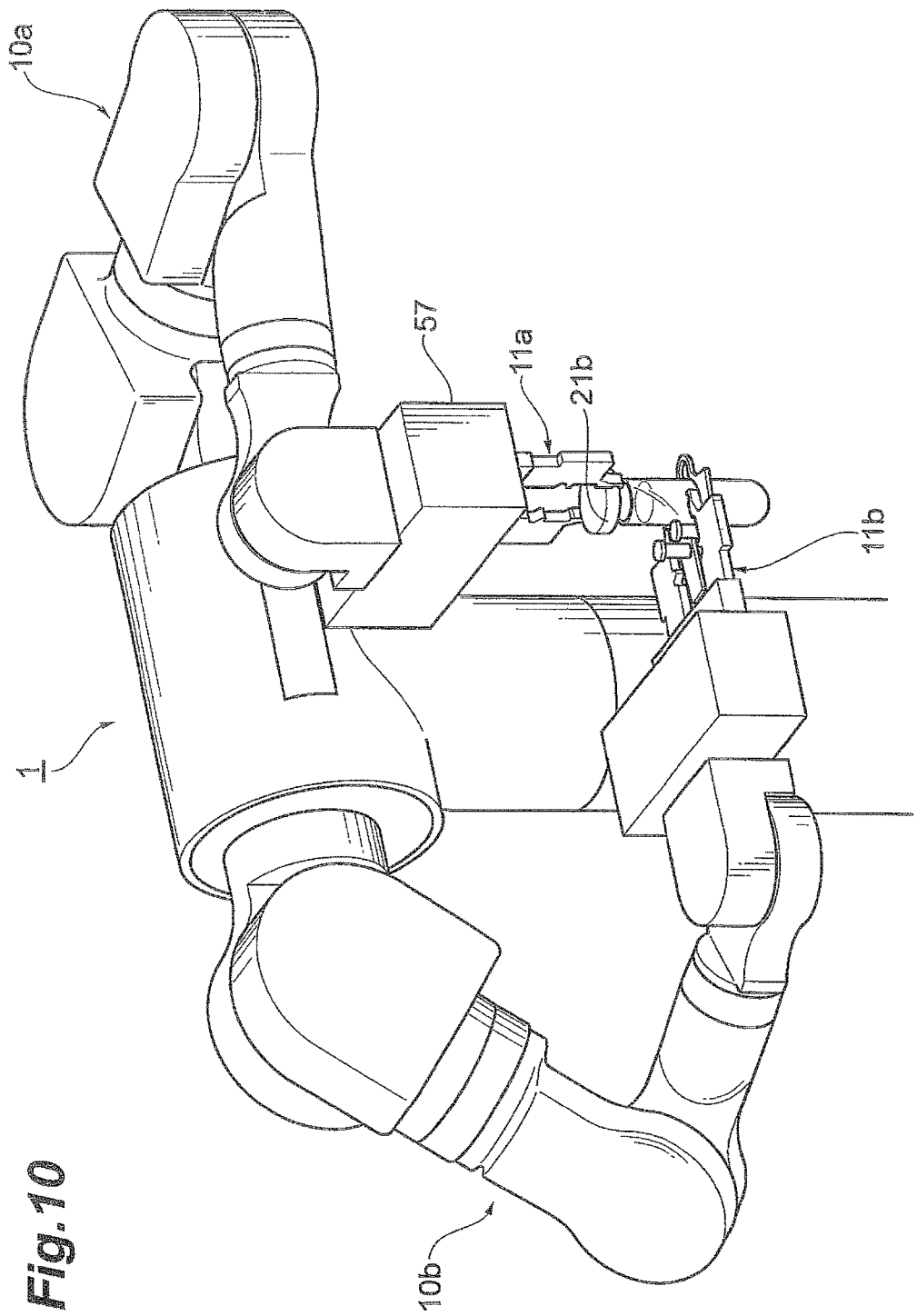
FIG. 10 is a perspective view illustrating the robot system during the normal control.

The initial control unit 12b and the normal control unit 12c control operation of the robots 10a and 10b by outputting operation instructions related to the opening processing to the robots 10a and 10b. The initial control unit 12b and the normal control unit 12c output an operation instruction to the robot 10b causing the robot 10b to keep the conical tube 21 at the predetermined operation position during the opening processing. The processing of the initial control unit 12b and the normal control unit 12c will be described also with reference to FIGS. 7 to 10. FIGS. 7 and 8 are perspective views of the robot system 1 during initial control. FIGS. 9 and 10 are perspective views of the robot system during normal control.

The initial control unit 12b outputs an operation instruction to the robot 10a causing the hand 11a to hold the screw cap 21b in a first attitude. In the first attitude, the first concave portions 113 of the hand 11a are in contact with the screw cap 21b (see FIG. 7). In this case, in the first attitude, the hand 11a holds the screw cap 21b in the horizontal direction. Specifically, in the first attitude is an attitude, the hand 11a holds the screw cap 21b in a state where the axes of the holding members 112 of the hand 11a are orthogonal to the axis of the conical tube 21. Since the bottoms 113a of the first concave portions 113 have long flat portions as described above, a surface in contact with the screw cap 21b is large, enabling effective application of force on the screw cap 21b. In addition, the corners of the first concave portions 113 engage with the outer surface of the screw cap 21b, enabling effective application of force on the screw cap 21b.

The initial control unit 12b outputs an operation instruction to the robot 10a causing the robot 10a to rotate the hand 11a in the above-described first attitude. Specifically, the initial control unit 12b rotates the hand 11a, etc. around a center 21c of the screw cap 21b by driving the seventh joint J7, the sixth joint J6, the fifth joint J5, and the fourth joint J4 in conjunction (see FIGS. 2B, 7, and 8).

The initial control unit 12b controls the hand 11a holding the screw cap 21b to rotate by about 30 to 60 degrees. The initial control unit 12b controls the hand 11a to rotate as described above twice, for example. More specifically, after the first rotation is completed, the initial control unit 12b outputs an operation instruction to the robot 10a causing the robot 10a to release the holding of the screw cap 21b and move the hand 11a back to the initial attitude of the rotation. Then, the initial control unit 12b outputs an operation instruction to the robot 10a causing the robot 10a to hold the screw cap 21b and rotate the hand 11a.

After the hand 11a is rotated in response to the operation instruction from the initial control unit 12b, the normal control unit 12c outputs an operation instruction to the robot 10a causing the hand 11a to hold the screw cap 21b in a second attitude. The second attitude is different from the above-described first attitude. Specifically, in the second attitude, the claws 115 of the hand 11a are in contact with the screw cap 21b (see FIG. 9). In the second attitude, the hand 11a holds the screw cap 21b in the vertical direction. Specifically, in the second attitude, the rotation axis Ax7, which is closest to the distal end side of the robot 10a, and the rotation axis AxS of the screw cap 21b coincide with each other (see FIG. 9). In other words, in the second attitude, the hand 11a holds the screw cap 21b in a state where the axes of the holding members 112 of the hand 11a are parallel to the axis of the conical tube 21.

The normal control unit 12c outputs an operation instruction to the robot 10a causing the hand 11a to rotate in the above-described second attitude. Specifically, the normal control unit 12c rotates the flange 57 around the rotation axis Ax7. In this case, the distance from the center of the screw cap 21b in the horizontal direction to the outer peripheral surface of the hand body 112a of the hand 11a is a rotation radius of the rotation operation. Thus, the flange 57 and the hand 11a driven by the flange 57 rotate integrally (see FIG. 9). The rotation radius is shorter than the rotation radius of rotation in the first attitude (i.e., an area of the outside interfered is small during operation). In addition, the rotation of the screw cap 21b is produced by driving only one joint (the seventh joint J7) at a high speed in the second attitude, while the rotation is produced by resultant force of the plurality of joints driven simultaneously in the first attitude.

The normal control unit 12c controls the hand 11a holding the screw cap 21b to rotate by about 160 to 200 degrees. When the rotation operation in the second attitude is completed, the tightening of the screw cap 21b onto the storage part 21a is completely released. Thus, after the rotation operation in the second attitude is completed, the normal control unit 12c moves the hand 11a holding the screw cap 21b upward (see FIG. 10) to complete the opening processing.

Figure 11:
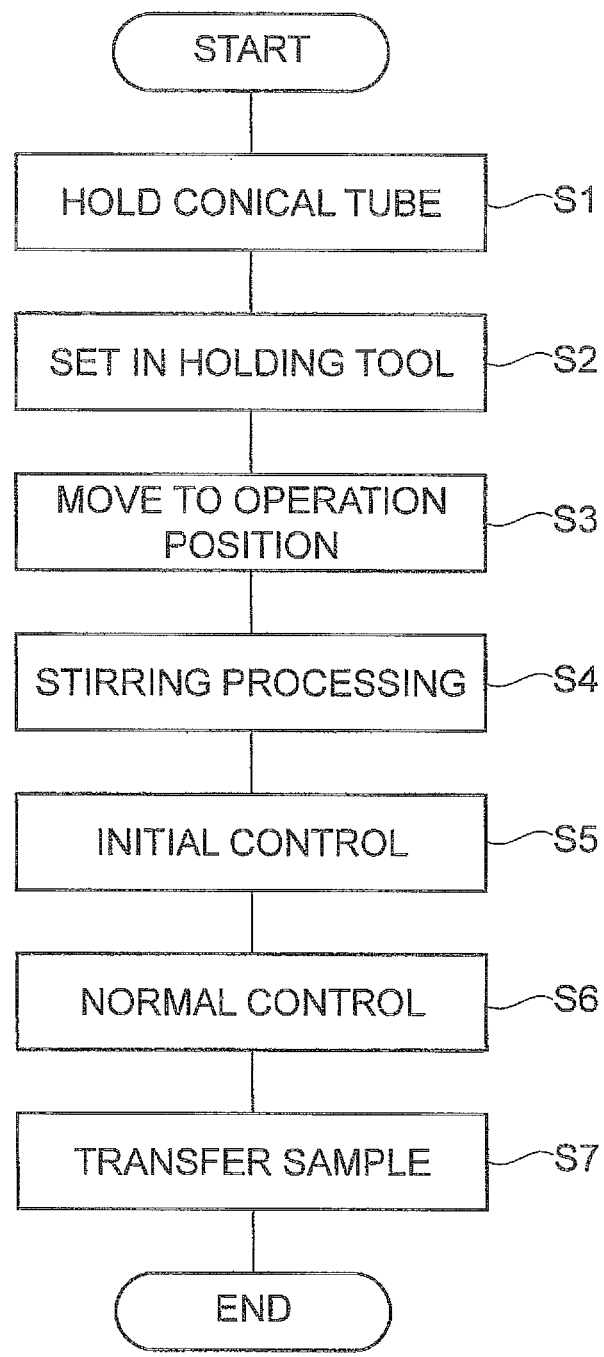
FIG. 11 is a flowchart illustrating procedures of opening operation.

Next, procedures of the opening operation will be described with reference to FIG. 11. FIG. 11 is a flowchart illustrating the procedures of the opening operation. First, based on the operation instruction of the control unit 12a, the robot 10b holds the conical tube 21 (step S1). Next, based on the operation instruction of the control unit 12a, the robot 10b sets the conical tube 21 in the holding tool 23 (step S2). In following steps, the robot 10b holds the conical tube 21 using the holding tool 23.

Next, based on the operation instruction of the control unit 12a, the robot 10b keeps the conical tube 21 at the predetermined operation position (step S3). Next, based on the operation instruction of the control unit 12a, the robot 10b performs the stirring processing of a sample 50 stored in the conical tube 21 (step S4).

Next, based on the operation instruction of the initial control unit 12b, the hand 11a holds the screw cap 21b in the first attitude (step S5, initial control step). Then, based on the operation instruction of the initial control unit 12b, the hand 11a holding the screw cap 21b in the first attitude rotates the screw cap 21b in the first attitude (step S5, initial control step).

Next, based on the operation instruction of the normal control unit 12c, the hand 11a holds the screw cap 21b in the second attitude (step S6, normal control step). Then, based on the operation instruction of the normal control unit 12c, the hand 11a holding the screw cap 21b in the second attitude rotates the screw cap 21b in the second attitude (step S6, normal control step).

Then, after the rotation operation in the second attitude is completed, the hand 11a holding the screw cap 21b moves upward based on the operation instruction of the normal control unit 12c, completing the opening processing. After the opening processing is completed, the robot 10b transfers the sample 50 stored in the conical tube 21 to the storage container 22 based on the operation instruction of the control unit 12a (step S7). Then, the screw cap 21b is tightened onto the conical tube 21 after the transfer of the sample again, and the conical tube 21 after the transfer of the sample 50 is moved back to the position of the conical tube 21 before the opening processing, completing a series of the opening operation. In addition, with the above-described operation, a method of manufacturing the conical tube 21 including the storage part 21a and the screw cap 21b is finished.

Next, effects of the robot system 1 according to the present embodiment will be described.

Usually, in an opening operation for opening a screw cap attached to a predetermined container, larger rotational force is required in the initial rotation compared with that in the following normal rotation. On the other hand, at the normal rotation, large rotational force required in the initial rotation is not required but more quick opening operation is required. In the robot system 1 and the opening method according to the present embodiment, the hand 11a is in different rotation attitudes in the initial rotation and the normal rotation. Specifically, the hand 11a is brought to the first attitude that can apply relatively large rotational force in the initial rotation, and to the second attitude that can rotate the screw cap 21b at a high speed in the normal rotation. As described above, the hand 11a is rotated in different attitudes in stages of the opening operation, enabling appropriate operation corresponding to the stages. Thus, failure of opening in the initial rotation is suppressed and the opening operation in the following normal rotation can be quickly performed at the same time.

In addition, in the robot system 1 and the opening method according to the present embodiment, the initial control unit 12b rotates the hand 11a by driving the plurality of joints: the seventh joint J7, the sixth joint J6, the fifth joint J5, and the fourth joint J4 simultaneously, and the normal control unit 12c rotates the hand 11a by driving only one joint: the seventh joint J7. Thus, the plurality of joints is driven simultaneously in the initial rotation, enabling to enlarge the rotational force, and the only one joint is driven in the normal rotation, enabling to perform the opening operation quickly.

In addition, in the robot system 1 and the opening method according to the present embodiment, rotational force can be appropriately applied to the screw cap 21b since each of the hands 11a and 11b has the pair of holding member 112, the relative distance of which can be increased/decreased (adjusted).

In addition, in the robot system 1 and the opening method according to the present embodiment, positions and angles at which the screw cap 21b and the hand 11a come in contact with each other are different in the first attitude and the second attitude. Specifically, in the first attitude in the initial rotation controlled by the initial control unit 12b, the first concave portions 113 of the hand 11a come in contact with the screw cap 21b and the hand 11a holds the screw cap 21b in the horizontal direction. Since the hand 11a comes in contact with the screw cap 21b at the bottom 113a of the first concave portions 113 having the long flat portions, the surface of the hand 11a in contact with the screw cap 21b can be large, enabling effective application of rotational force on the screw cap 21b. Further, since the corners of the first concave portions 113 engage with the outer peripheral surface of the screw cap 21b, rotational force can be effectively applied on the screw cap 21b. Then, the hand 11a holds the screw cap 21b in the horizontal direction, enabling to hold the screw cap 21b by the first concave portions 113 smoothly. On the other hand, in the second attitude in the normal rotation controlled by the normal control unit 12c, the claws 115 of the hand 11a are in contact with the screw cap 21b, and the hand 11a holds the screw cap 21b in the vertical direction. Then, the hand 11a holds the screw cap 21b in the vertical direction, enabling the quick opening operation only with the seventh joint J7 driven as described above.

In addition, in the robot system 1 and the opening method according to the present invention, the control unit 12a controls the operation of the robot 10b to hold the conical tube 21 with the hand 11b and keep the conical tube 21 at the predetermined operation position, enabling the opening operation described above.

In the robot system 1 and the opening method according to the present embodiment, the hand 11b holds the conical tube 21 using the holding tool 23, suppressing damage on the conical tube 21.

In the robot system 1 and the opening method according to the present embodiment, the robot system 1 further includes the body 13, to which the robot 10a and the robot 10b are attached, and the body 13 is configured to support the robot 10a and the robot 10b, improving the interlocking relationship of operation of the two robots.

In the robot system 1 and the opening method according to the present embodiment, a seven-axis robot having seven degrees of freedom, which is the same as the human body, is used as the robot 10a, whereby a robot can realize movement closer to a human.

One embodiment of the present invention has been described above, but the invention is not limited to the embodiment. For example, in the above description of the robot system 1 according to the present embodiment, positions and angles at which the screw cap 21b and the hand 11a come in contact with each other are different in the first attitude in the initial rotation controlled by the initial control unit 12b and in the second attitude in the normal rotation controlled by the normal control unit 12c. However, the first attitude and the second attitude are not limited thereto and either one of positions or angles at which the screw cap and the hand come in contact with each other may be different. In addition, both of positions and angles at which the screw cap and the hand come in contact with each other may be the same in the first attitude and in the second attitude.

In addition, in the above description, the robot system 1 includes the robot 10a and the robot 10b, however, only a robot provided with a hand for holding a screw cap is necessary and a robot for fixing a conical tube (the robot 10b in the present embodiment) is not necessary. The opening operation can be performed by only a robot provided with a hand for holding a screw cap when a conical tube is fixed at a predetermined fixing position.

Indeed, the novel devices and methods described herein may be embodied in a variety of other forms; furthermore, various omissions, substitutions and changes in the form of the devices and methods described herein may be made without departing from the spirit of the inventions. The accompanying claims and their equivalents are intended to cover such forms or modification as would fall within the scope and spirit of the inventions.

Certain aspects, advantages, and novel features of the embodiment have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

What is claimed is:

1. A robot system comprising:
   a first robot;
   a first hand comprising:
      a hand body attached to the first robot; and
      holding members extending from the hand body in an extending direction to hold a screw cap tightened onto a container therebetween, the holding members each having a concave portion such that the concave portions of the holding members face each other; and
   a control device configured to control an operation of the first robot, wherein the control device includes:
      an initial control unit programmed to rotate the first hand about a center axis of the screw cap in a state where the holding members of the first hand hold the screw cap in a first attitude in which the extending direction is at a first angle with respect to the center axis of the screw cap; and
      a normal control unit programmed to rotate the first hand about the center axis in a state where the holding members of the first hand hold the screw cap in a second attitude different from the first attitude after the first hand is operated by the initial control unit, wherein, in the second attitude, the extending direction is at a second angle with respect to the center axis of the screw cap, the second angle being different from the first angle,
   wherein the control device is configured to control the operation of the first robot such that the screw cap is in contact with a first surface area on the concave portions of the holding members of the first hand in the first attitude and such that the screw cap is in contact with a second surface area of the holding members on the first hand in the second attitude, the first surface area being larger than the second surface area.

2. The robot system according to claim 1, wherein
   the first robot includes a plurality of joints capable of being rotary driven,
   the initial control unit is configured to rotate the first hand by driving the plurality of joints simultaneously, and
   the normal control unit is configured to rotate the first hand by driving one of the joints.

3. The robot system according to claim 2, wherein a distance between the holding members is adjustable.

4. The robot system according to claim 2, wherein the control device is configured to control the operation of the first robot such that the screw cap is in contact with a first position on the first hand in the first attitude and such that the screw cap is in contact with a second position on the first hand in the second attitude, the first position being different from the second position.

5. The robot system according to claim 1, wherein a distance between the holding members is adjustable.

6. The robot system according to claim 5, wherein the control device is configured to control the operation of the first robot such that the screw cap is in contact with a first position on the first hand in the first attitude and such that the screw cap is in contact with a second position on the first hand in the second attitude, the first position being different from the second position.

7. The robot system according to claim 1, wherein the control device is configured to control the operation of the first robot such that the screw cap is in contact with a first position on the first hand in the first attitude and such that the screw cap is in contact with a second position on the first hand in the second attitude, the first position being different from the second position.

8. The robot system according to claim 1, further comprising:
a second robot; and
a second hand attached to the second robot, wherein
the control device is configured to control operation of the second robot to cause the second hand to hold the container and to keep the container at an operation position.

9. The robot system according to claim 8, wherein the first robot is a seven-axis robot.

10. The robot system according to claim 8, further comprising a common body to which the first robot and the second robot are attached.

11. The robot system according to claim 10, wherein the first robot is a seven-axis robot.

12. The robot system according to claim 8, wherein the second hand holds the container using a holding tool.

13. The robot system according to claim 12, further comprising a common body to which the first robot and the second robot are attached.

14. The robot system according to claim 13, wherein the first robot is a seven-axis robot.

15. The robot system according to claim 12, wherein the first robot is a seven-axis robot.

16. The robot system according to claim 1, wherein the first robot is a seven-axis robot.

17. The robot system according to claim 1,
wherein the extending direction is substantially orthogonal to the axial direction in the first attitude, and
wherein the extending direction is substantially parallel to the axial direction in the second attitude.

18. The robot system according to claim 1, further comprising:
a flange connected to the hand body and rotatably supported by the first robot, wherein
the normal control unit is configured to rotate the flange about the center axis of the screw cap in the second attitude.

19. A container opening method comprising:
rotating a first hand, which is attached to a first robot and comprising holding members extending in an extending direction, in a state where the holding members of the first hand hold a screw cap tightened onto a container, about a rotation axis of the screw cap in a first attitude in which the extending direction is at a first angle with respect to the rotation axis of the screw cap; and thereafter rotating the first hand in a state where the holding members of the first hand hold the screw cap in a second attitude different from the first attitude, wherein, in the second attitude, the extending direction is at a second angle with respect to the rotation axis of the screw cap, the second angle being different from the first angle.

20. A manufacturing method of an object to be processed including a container body and a screw cap tightened onto the container body, the method comprising:
rotating a first hand, which is attached to a first robot and comprising holding members extending in an extending direction, in a state where the holding members of the first hand hold the screw cap, about a rotation axis of the screw cap in a first attitude in which the extending direction is at a first angle with respect to the rotation axis of the screw cap; and thereafter rotating the first hand in a state where the holding members of the first hand hold the screw cap in a second attitude different from the first attitude, wherein, in the second attitude, the extending direction is at a second angle with respect to the rotation axis of the screw cap, the second angle being different from the first angle.

* * * * *